United States Patent [19]
Patel

[11] Patent Number: 5,852,180
[45] Date of Patent: Dec. 22, 1998

[54] CHEMICAL SYNTHESIS OF 6-O-ALKYL ERYTHROMYCIN A

[75] Inventor: Hemantkumar H. Patel, Gurnee, Ill.

[73] Assignee: Abbott Laboratories, Abbott Park, Ill.

[21] Appl. No.: 972,155

[22] Filed: Nov. 17, 1997

[51] Int. Cl.$^6$ ............................. C07H 1/00; C07H 17/08
[52] U.S. Cl. ..................... 536/7.4; 536/18.5; 536/18.6
[58] Field of Search ................................ 536/7.4, 18.5, 536/18.6

[56] References Cited

U.S. PATENT DOCUMENTS

| | | | |
|---|---|---|---|
| 4,331,803 | 5/1982 | Watanabe et al. | 536/7.2 |
| 4,668,776 | 5/1987 | Yamada et al. | 536/7.4 |
| 4,670,549 | 6/1987 | Morimoto et al. | 536/7.4 |
| 4,672,109 | 6/1987 | Watanabe et al. | 536/7.2 |
| 4,680,386 | 7/1987 | Morimoto et al. | 536/7.4 |
| 4,990,602 | 2/1991 | Morimoto et al. | 536/7.4 |
| 5,274,085 | 12/1993 | Amano et al. | 536/7.4 |

FOREIGN PATENT DOCUMENTS

0260938 A2 3/1988 European Pat. Off. .

*Primary Examiner*—Elli Peselev
*Attorney, Agent, or Firm*—Mona Anand

[57] ABSTRACT

A process of preparing 6-O-alkyl erythromycin A is provided. The process includes the steps of protecting the oxime hydroxyl of 9-oxime erythromycin A with a benzoyl protecting group, protecting the 2'-hydroxyl group and optionally the 4'-hydroxyl group with an O-protecting group, alkylating the 6-hydroxyl, removing the benzoyl and O-protecting groups and deoximating the 9-oxime.

14 Claims, No Drawings

CHEMICAL SYNTHESIS OF 6-O-ALKYL ERYTHROMYCIN A

DESCRIPTION

1. Technical Field of the Invention

The present invention relates to erythromycin derivatives. More particularly, the present invention pertains to a process for the chemical synthesis of 6-O-alkyl erythromycin A.

2. Background of the Invention

6-O-methyl erythromycin A (Clarithromycin), shown below, is a potent macrolide antibiotic (U.S. Pat. No. 4,331,803).

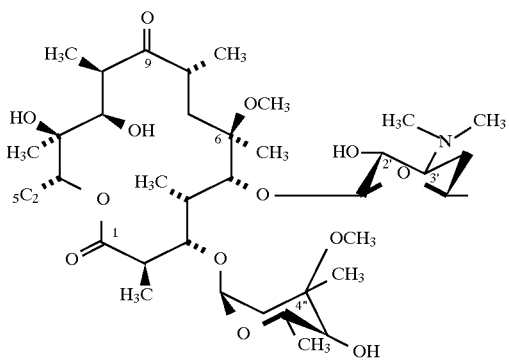

A variety of means for preparing 6-O-methyl erythromycin A have been described. 6-O-methyl erythromycin A can be prepared by methylating a 2'-O-3'-N-dibenzyloxycarbonyl-des-N-methyl derivative of erythromycin A (U.S. Pat. No. 4,331,803). 6-O-methyl erythromycin A can also be made from 9-oxime erythromycin A derivatives (See, e.g., U.S. Pat. Nos. 5,274,085; 4,680,386; 4,668776; 4,670,549 and 4,672,109 and European Patent Application 0260938 A2).

In those processes utilizing 9-oxime erythromycin A derivatives, the oxime is protected during methylation with a 2-alkenyl group (U.S. Pat. Nos. 4,670,549 and 4,668,776), a benzyl or substituted benzyl group (U.S. Pat. Nos. 4,680,386, and 4,670,549) or a moiety selected from the group consisting of lower alkyl, substituted alkyl, lower alkenyl, aryl substituted methyl, substituted oxalkyl, and substituted thiomethyl (U.S. Pat. No. 4,672,109). U.S. Pat. No. 4,990,602 discloses derivatizing the 9-oxime hydroxyl group before alkylating the 6-OH group. This is the commercial method currently used in the manufacture of clarithromycin.

There are drawbacks to the existing methods for producing 6-O-methyl erythromycin A. By way of example, failure to protect the 2'-OH group leads to undesired methylation of that group. Existing methods for protecting the 2'-OH group are unsatisfactory because those methods also require protection of the 3'-nitrogen. U.S. Pat. No. 4,680,386 discloses protection of the 2'-OH group with a benzyloxy carbonyl moiety. Under such circumstances, however, the 3'-nitrogen also undergoes N-demethylation followed by N-benzyloxy carbonyl formation. This 3'-N-benzyloxy carbonyl group must be deprotected following 6-O-methylation. The 3'-dimethylamino group is regenerated following 6-O-methylation by N-methylation. U.S. Pat. No. 4,670,549 discloses protection of the 2'-OH group as a benzyl or like substituent. Under these circumstances, the 3'-nitrogen group must also be protected as a quaternary salt. This quaternary salt must be removed following 6-O-methylation to regenerate the 3'-dimethyl amino group. Deprotection of 9-oxime derivatives protected with oxyalkyl groups has to be carried out in harsh conditions, which lead to undesired side product formation. By way of further example, the use of benzyloxycarbonyl groups for protection of the 2'-hydroxy group (U.S. Pat. No. 4,311,803) requires large amounts of benzyl chloroformate, which is severely irritating and toxic. By way of still further example, there are the problems in protecting the oxime with benzyloxycarbonyl. The group is too unstable during methylation under alkaline conditions.

There continues to be a need to provide a rapid, efficient method of producing 6-O-methyl erythromycin A that uses mild, neutral synthetic conditions.

BRIEF SUMMARY OF THE INVENTION

The present invention provides an efficient and practical method of synthesizing 6-O-alkyl erythromycin A, known in the art as Clarithromycin. The synthetic process uses 1) benzoyl protecting groups for protection of the 9-oxime functionality and 2) O-protecting groups for the 2'- or 2'- and 4"-hydroxyl groups during selective alkylation of the 6-hydroxyl derivative of erythromycin A.

The synthetic process begins with erythromycin A oxime, obtained by any method. The 9-oxime group of erythromycin A is protected using a benzoyl protecting group. Protection is accomplished by reacting erythromycin A oxime with a benzoylating reagent of the formula RCOX, where X is halide and R is a di-substituted benzene with the substituent groups being Cl, Br, I or alkoxy.

Prior to alkylation of the 6-hydroxyl group, the 2'-hydroxyl or the 2'- and 4"-hydroxyl groups are O-protected. Where both the 2'- and 4"-hydroxyl groups are protected, the preferred protecting group is a trimethylsilyl group. Hexamethyldisilazane is used as a preferred silylating reagent. Use of non-trimethylsilyl protecting groups obviates the need to protect the 4"-hydroxyl group. Oxime protection and O-protection of the 2'- and 4"-hydroxyl groups can occur in any order. Preferably, protection of the oxime occurs after O-protection of the 2'- and 4"-hydroxyl groups.

The oxime protected, 2'-protected or 2',4"-diprotected erythromycin A derivative is then alkylated using alkylating reagents well known in the art. Preferred alkylating reagents are alkyl halides. The protecting groups are removed using alcoholic alkali metal carbonates. Deoximation is carried out using standard procedures well known to art to provide 6-O-alkyl erythromycin A.

DETAILED DESCRIPTION OF THE INVENTION

A number of defined terms are used herein to designate particular elements of the present invention. When so used, the following meanings are intended:

The term "alkyl" refers to saturated, straight or branched-chain hydrocarbon radicals containing between one and ten carbon atoms including, but not limited to, methyl, ethyl, propyl, isopropyl, n-butyl, tert-butyl and neopentyl. Preferably, alkyl is limited to 1–4 carbons.

The term "alkylating agent" refers to a reagent capable of placing an alkyl group onto a nucleophilic site, including, but not limited to, alkyl halides such as methyl bromide, ethyl bromide, n-propyl bromide, methyl iodide, ethyl iodide; and n-propyl bromide; dialkyl sulfates such as dimethyl sulfate, diethyl sulfate; and di-n-propyl sulfate; and alkyl or aryl sulfonates such as methyl-p-toluenesulfonate, ethyl methanesulfonate, n-propyl methanesulfonate, and the like.

The term "aryl(lower alkyl)" refers to a lower alkyl radical having appended thereto 1–3 aromatic hydrocarbon groups, as for example benzyl, diphenylbenzyl, trityl and phenylethyl.

The term "aryloxy" refers to an aromatic hydrocarbon radical which is joined to the rest of the molecule via an ether linkage (i.e., through an oxygen atom), as for example phenoxy.

The term "cycloalkyl" refers to a saturated monocyclic hydrocarbon radical having from three to eight carbon atoms in the ring and optionally substituted with between one and three additional radicals selected from among lower alkyl, halo(lower alkyl), lower alkoxy, and halogen. Examples of cycloalkyl radicals include, but are not limited to, cyclopropyl, cyclobutyl, cyclopentyl, cyclohexyl, cycloheptyl, 1-fluoro-cyclopropyl, and 2-fluorocyclopropyl.

The term "lower alkenyl" refers to a straight or branched-chain hydrocarbon radical containing between two and six carbon atoms and possessing at least one carbon-carbon double bond. Examples of lower alkenyl radicals include vinyl, allyl, 2- or 3-butenyl, 2-, 3- or 4-pentenyl, 2-, 3-, 4- or 5-hexenyl and isomeric forms thereof.

The term "lower alkoxy" refers to a lower alkyl radical which is joined to the rest of the molecule via an ether linkage (i.e., through an oxygen atom). Examples of lower alkoxy radicals include, but are not limited to, methoxy and ethoxy.

The term "lower alkyl" refers to an alkyl radical containing one to six carbon atoms including, but not limited to, methyl, ethyl, propyl, isopropyl, n-butyl, tert-butyl and neopentyl.

The term "polar aprotic solvent" refers to polar organic solvents lacking an easily removable proton, including, but not limited to, N,N-dimethylformamide, dimethyl sulfoxide, N-methyl-2-pyrrolidone, hexamethylphosphoric triamide, tetrahydrofuran, 1,2-dimethoxyethane, acetonitrile or ethyl acetate, and the like.

The term "silyl" refers a group of the formula $Si(R^1)(R^2)(R^3)$ where each of $R^1$, $R^2$ and $R^3$ are independently hydrogen, lower alkyl, aryl, phenyl, phenylsubstituted lower alkyl, cycloalkyl or alkenyl.

The term "strong alkali metal base" refers to an alkali metal base having a weak conjugate acid, including, but not limited to, sodium hydroxide, potassium hydroxide, sodium hydride, potassium hydride, potassium t-butoxide, and the like.

The term "substituted aryl(lower alkyl)" refers to an aryl(lower alkyl) residue as defined above having between one and three non-hydrogen ring substituents, each independently selected from among halogen, lower alkoxy, lower alkyl, hydroxy-substituted lower alkyl, and (lower alkyl)amino. Examples of substituted aryl(lower alkyl) radicals include 2-fluorophenylmethyl, 4-fluorophenylethyl and 2,4-difluorophenylpropyl.

The term "weak organic amine base" refers to an organic amine base having a strong conjugate acid, including, but not limited to trimethylamine, triethylamine, tripropylamine, pyridine, 2-methoxypyridine, 1-methylpyrrolidine, 1-methylpiperidine, and 1-ethylpiperidine, and the like.

The present invention provides a process of preparing 6-O-alkyl erythromycin A. The process begins with 9-oxime erythromycin A. 9-Oxime erythromycin A can be obtained from any source. Preferably, 9-oxime erythromycin A is made by oximating erythromycin A using standard procedures well known in the art (See e.g., U.S. Pat. No. 5,274,085, the disclosure of which is incorporated herein by reference ). For example, erythromycin A, obtained from fermentation, can be reacted with either hydroxylamine hydrochloride and a base, free hydroxylamine in methanol or hydroxylamine and an organic acid. Preferably, oximation of erythromycin A is accomplished using hydroxylamine and formic acid.

Prior to selectively alkylating the 6-hydroxyl group of 9-oxime erythromycin A, it is necessary to protect other hydroxyl groups in the compound. Those other hydroxyl groups are the oxime hydroxyl (N—OH), the 2'-hydroxyl and optionally the 4"-hydroxyl. Protection of those hydroxyl groups can be accomplished in any order so long as all groups are protected prior to alkylation of the 6-hydroxyl.

In one embodiment, 9-oxime erythromycin A is first protected at the oxime hydroxyl by reacting the oxime with a benzoylating reagent. A suitable reagent has the formula RCOX, where X is halide and R is a di-substituted benzene. Preferably, X is chloride. The two substitutions in benzene are preferably located at the 2 and 4 or 2 and 6 carbons. Any substituent group that does not interfere with subsequent reactive steps can be used. Preferably, the substituent group is an alkoxy, chloride, bromide or iodide. Preferred alkoxy groups are ethoxy and methoxy. Exemplary and preferred benzoylating reagents are thus componds of the formula RCOX, where X is chloride and R is 2,6-dichlorobenzene, 2,6-dibromobenzene, 2,6-diiodobenzene, 2,6-dimethoxybenzene, 2,6-diethoxybenzene 2,4-dichlorobenzene, 2,4-dibromobenzene, 2,4-diiodobenzene, 2,4-dimethoxybenzene or 2,4-diethoxybenzene.

In one embodiment, both the 2'- and 4"-hydroxyl groups are protected. Protection of those hydroxyl goups is accomplished using a silyl group. Exemplary and preferred silyl groups have the formula:

where $R^1$, $R^2$, and $R^3$ are each independently hydrogen, lower alkyl, aryl, phenyl, phenyl substituted lower alkyl, cycloalkyl or alkenyl. Preferably, all of $R^1$, $R^2$ and $R^3$ are methyl. Silyl groups can be positioned at the 2'- and 4"-hydroxyl groups using standard procedures well known in the art. By way of example, a trimethyl silyl group can be positioned at the 2'- and 4"-positions by reacting a 9-oxime erythromycin A derivative (oxime protected or unprotected) with the silylating agent hexamethyldisilazane (HMDS) in the presence of acid (e.g., $HCO_2H$). This same transformation can be carried out using other silylating agents such as trimethylsilylchloride (TMSchloride) in the presence of an organic base such as $Et_3N$, pyridine, or imidazole. Other silylation conditions can also be used. Such conditions typically include the use of a suitable solvent such as acetonitrile ($CH_3CN$).

In another embodiment, it is only neccesary to protect the 2'-hydroxyl group. (See U.S. patent application Ser. No. 627,795, filed Apr. 2, 1996, incorporated herein by reference). Such protection can be accomplished using conventional O-protecting groups well known in the art. Exemplary and preferred O-protecting groups are alkoxycarbonyls (e.g., methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethyl-hexyloxycarbonyl, cyclohexyloxycarbonyl, methyloxycarbonyl and the like), alkoxyalkoxycarbonyls (e.g., methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxy- methoxycarbonyl and the like), haloalkoxycarbonyls (e.g., 2-chloroethoxycarbonyl, 2-chloroethoxycarbonyl, 2,2,2-trichloro- ethoxycarbonyl and the like), unsaturated alkoxycarbonyls (e.g., allyloxycarbonyl, pro-pargyloxycarbonyl, 2-butenoxycarbonyl, 3-methyl 2-butenoxycarbonyl and the like), substituted benzyloxycarbonyls (e.g., benzyloxycarbonyl, p-methylbenzyloxycarbonyl, p-methoxy benzyloxycarbonyl, p-nitro-benzyloxycarbonyl, 2,4-dinitrobenzyloxycarbonyl, 3,5-dimethyl-benzyloxycarbonyl, p-chlorobenzyloxycarbonyl, p-bromobenzyloxycarbonyl and the like) and substituted phenoxycarbonyls [e.g., phenoxycarbonyl, p-nitrophenoxycarbonyl, o-nitrophenoxycarbonyl, 2,4-dinitrophenoxycarbonyl, p-methylphenoxycarbonyl, m-methylphenoxy- carbonyl, o-bromophenoxycarbonyl, 3,5-dimethylphenoxycarbonyl, p-chlorophenoxycarbonyl, 2-chloro 4-nitrophenoxycarbonyl and the like (See e.g., Greene and Wuts' *Protective Groups in Organic Synthesis*, 2d. Ed. John Wiley & Sons, Inc., New York, 1991., the disclosure of which is incorporated herein by reference).

Exemplary and preferred lower alkyl monocarbonyl groups are acetyl, propionyl, butyryl, isobutyryl and the like. Exemplary and preferred lower alkenyl monocarbonyl groups include acryloxyl, methacryloxy and the like. Exemplary and preferred lower alkoxycarbonyl-alkylcarbonyl groups include methoxycarbonyl-methylcarbonyl, ethoxycarbonylmethylcarbonyl, ethoxycarbonyl-ethylcarbonyl and the like. Exemplary and preferred arylcarbonyl groups include benzoyl, p-methoxybenzoyl, 3,4,5-trimethoxybenzoyl, p-chlorobenzoyl, 2,4-dichlorobenzoyl, 3,5 -dichlorobenzoyl, diphenylacetyl, 1-naphthaleneacetyl, 2-naphthaleneacetyl and the like.

The use of O-protecting groups in the preparation of erythromycin derivatives has been described (See e.g., U.S. Pat. No. 4,672,109, and European Patent Application 0260938A2, the disclosures of which are incorporated herein by reference). Conventional O-protecting groups, as set forth above, are positioned using standard procedures well known in the art. By way of example, an acetyl group can be positioned at the 2'-position by reacting an erythromycin A derivative (9-oxime or 9-oximesilyl) with an acetylating agent and a base. Suitable acetylating agents that can be used include anhydride and acid halide compounds of the formula $(R^4CO)_2O$ or $R^4COCl$, where $R^4$ is hydrogen or a substituent group such as lower alkyl (e.g., methyl, ethyl, n-propyl, isopropyl, n-butyl, sec-butyl, t-butyl and the like) or aryl (e.g., phenyl, p-methoxyphenyl, p-chlorophenyl, m-chlorophenyl, o-chlorophenyl, 2,4,-dichlorophenyl, p-bromophenyl, m-nitrophenyl, p-nitrophenyl, benzhydryl, 1-naphthyl and the like). Suitable bases are organic bases such as triethylamine, pyridine and diethylamine.

One of skill in the art will readily appreciate that it may be advantageous to also substitute for a methyl group of the dimethylamino moiety at the 3'-position of erythromycin A using a conventional N-protecting group. Exemplary and preferred N-protecting groups are alkoxycarbonyl groups (e.g., a methoxycarbonyl group, an ethoxycarbonyl group, an isopropoxycarbonyl group, an n-propoxycarbonyl group, an n-butoxycarbonyl group, an isobutyloxycarbonyl group, a sec-butyloxycarbonyl group, a t-butyloxycarbonyl group, a 2-ethylhexyloxycarbonyl group, a cyclohexyloxycarbonyl group, a methyloxycarbonyl group and the like); alkoxy-alkoxycarbonyl groups (e.g., a methoxymethoxycarbonyl group, an ethoxymethoxycarbonyl group, a 2-methoxyethoxycarbonyl group, a 2-ethoxyethylcarbonyl group, a 2-ethoxyethoxycarbonyl group, a 2-butoxyethoxycarbonyl group, a 2-methoxyethoxy- methoxycarbonyl group and the like); haloalkoxycarbonyl groups (e.g., a 2-chloroethoxycarbonyl group, a 2-chloroethoxycarbonyl group, a 2,2,2-trichloroethoxycarbonyl group and the like), unsaturated alkoxycarbonyl groups (e.g., an allyloxycarbonyl group, a propargyloxycarbonyl group, a 2-butenoxycarbonyl group, a 3-methyl-2-butenoxycarbonyl group and the like), substituted benzyloxycarbonyl groups (e.g., a benzyloxycarbonyl group, a p-methylbenzyloxycarbonyl group, a p-methoxybenzyloxycarbonyl group, a p-nitrobenzyloxycarbonyl group, a 2,4-initrobenzyloxy -carbonyl group, a 3,5-dimethylbenzyloxycarbonyl group, a p-chlorobenzyloxycarbonyl group, a p-bromobenzyloxy-carbonyl group and the like), and substituted phenoxycarbonyl groups [e.g., a phenoxycarbonyl group, a p-nitrophenoxycarbonyl group, an o-nitrophenoxycarbonyl group, a 2,4-dinitrophenoxycarbonyl group, a p-methylphenoxycarbonyl group, an m-methylphenoxycarbonyl group, an o-bromophenoxycarbonyl group, a 3,5-dimethylphenoxycarbonyl group, a p-chloro-phenoxycarbonyl group, a 2-chloro-4-nitrophenoxycarbonyl group and the like (U.S. Pat. No. 4,672,109)].

As set forth hereinbefore, either the oxime hydroxyl group or the 2'- and 4"-hydroxyl groups can be protected first. The yield and purity of product formation, however, is improved when the oxime-hydroxyl group is protected after the 2'- and 4"-hydroxyl groups.

The 2', 4"-disilyl-9-oximebenzoyl erythromycin A or 2'-protected-9-benzoyl erythromycin A is then selectively alkylated at the 6-hydroxyl group. Procedures and reagents for alkylating the 6-hydroxyl group of erythromycin derivatives are well known in the art (See e.g., U.S. Pat. Nos. 4,672,109 and 4,670,549). Briefly, the protected-9-oximebenzoyl erythromycin A is reacted with a suitable alkylating agent in the presence of a base. Exemplary and preferred alkylating agents are alkyl halides or alkyl sulfates. In a preferred embodiment, the 6-hydroxyl group is methylated. Exemplary and preferred methylating reagents are methyl bromide, methyl iodide, dimethyl sulfate, and methyl-p-toluenesulfonate.

Exemplary and preferred bases are a strong alkali metal base, preferably selected from the group consisting of an alkali metal hydride, alkali metal hydroxide or alkali metal alkoxide, and a weak organic amine base, preferably selected from the group consisting of trimethylamine, triethylamine, tripropylamine, pyridine, 2-methoxypyridine, 1-methylpyrrolidine, 1-methylpiperidine, and 1-ethylpiperidine. Enhanced purity of selective methylation is found when less than about 1.5 equivalents of base are used.

The alkylation step is carried out in a suitable solvent. Exemplary and preferred solvents are polar aprotic solvents such as N,N-dimethylformamide, dimethyl sulfoxide, N-methyl-2-pyrrolidone, hexamethylphosphoric triamide, tetrahydrofuran, 1,2-dimethoxyethane, acetonitrile methyl-t-butyl or ethyl acetate, or a mixture of such polar aprotic solvents maintained at a reaction temperature and for a period of time sufficient to effect alkylation, preferably from −15° C. to room temperature for a period of 1 to 8 hours.

The preparation of 6-O-alkyl erythromycin A proceeds by removing the O-protecting groups from the 2'- and 4"-positions and the benzoyl group from the 9-oximebenzoyl group and then deoximating the 9-oxime. Means for removing the O-protecting groups at the 2'- and 4"-positions are well known in the art. By way of example, the silyl groups can be removed by reacting the silylated derivative with an alcoholic carbonate such as methanolic potassium carbonate. An advantage to the use of such a carbonate is that the benzoyl protecting group is simultaneously removed from the 9-oximebenzoyl group. As is well known in the art, removal of the silyl group can also be accomplished using (a) t-Bu$_4$NF in THF, (b) HOAc/THF/H$_2$O, (c) citric acid/MeOH, (d) Dowex resin/MeOH, K$_2$CO$_3$/MeOH, (e) n-Bu$_4$NCl/KF or (f) HF/CH$_3$CN.

A final step in the preparation of 6-O-alkyl erythromycin A is deoximation. Deoximation is carried out in accordance with standard procedures well known in the art (See e.g., U.S. Pat. No. 4,672,109). Briefly, the 9-oxime derivative is reacted with sodium hydrogen sulfite in alcohol (e.g., ethanol) and refluxed. The solution is cooled, alkalinized and precipitated with aqueous sodium bicarbonate. The precipitate formed in the above reaction is collected by filtration, washed and recrystallized with alcohol.

A detailed description of the synthesis of 6-O-methyl erythromycin A, using a process of the present invention is set forth hereinafter in the Examples. A schematic illustration of two embodiments of a synthetic scheme in accordance with the present invention is set forth in below in Scheme 1.

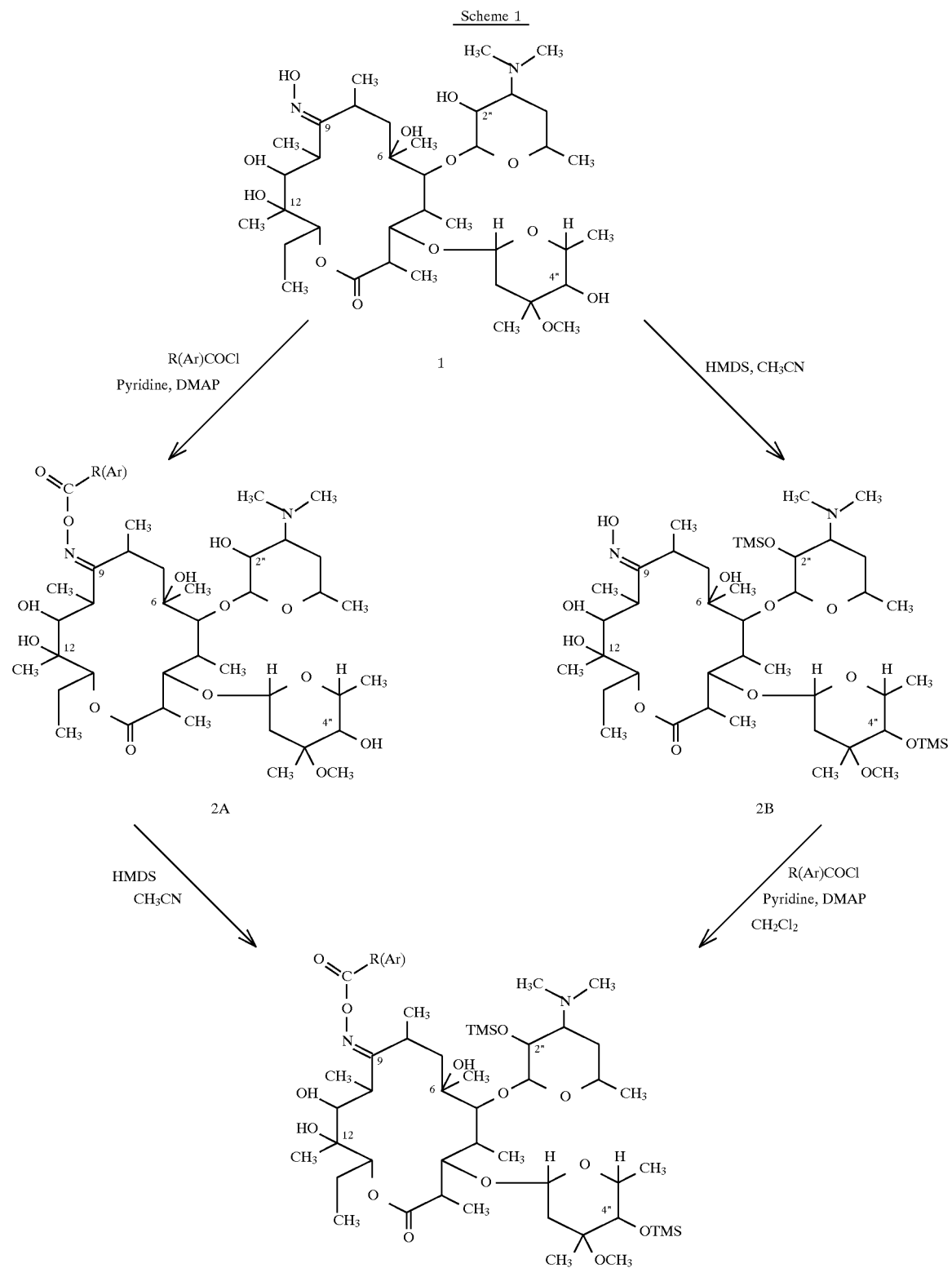

With reference to Scheme 1, 9-oxime erythromycin A (Compound 1) is reacted with either a benzoylating reagent [RCOCl] in the presence of pyridine and DMAP or with HMDS in acetonitrile to form Compound 2A (the oxime-protected derivative) or Compound 2B (the 2',4"-protected derivative), respectively.

Compound 2A is then reacted with HMDS in acetonitrile to form Compound 3. Alternately, Compound 2B is reacted with the benzylating reagent [RCOCl] in pyridine and DMAP to form Compound 3.

Compound 3 is then methylated, deprotected and de-oximated to provide 6-O-methyl erythromycin A.

In another aspect, the present invention provides certain intermediates formed during a process of this invention. Such intermediates correspond to structure I, below,

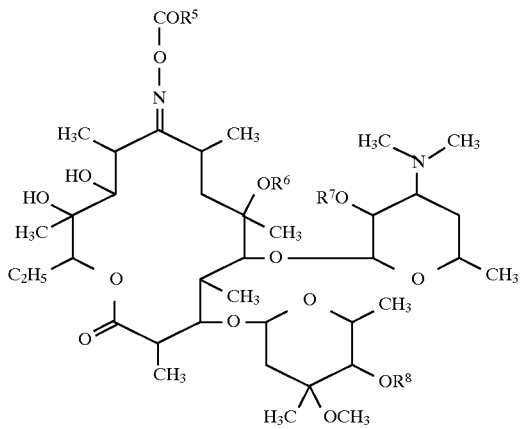

where $R^5$ is a disubstituted benzene, $R^6$ is hydrogen or alkyl and $R^7$ and $R^8$ are each independently hydrogen, trimethylsilyl or an O-protecting group. In a preferred embodiment, $R^6$ is methyl, and both $R^7$ and $R^8$ are trimethylsilyl. In another embodiment, $R^7$ is an O-protecting group and $R^8$ is hydrogen. Exemplary and O-protecting groups are the same as set forth above. In a preferred embodiment, $R^5$ is 2,6-dichlorobenzene, 2,6-dibromobenzene, 2,6-diiodobenzene, 2,6-dimethoxybenzene, 2,6-diethoxybenzene 2,4-dichlorobenzene, 2,4-dibromobenzene, 2,4-diiodobenzene, 2,4-dimethoxybenzene or 2,4-diethoxybenzene.

The following Examples illustrate preferred embodiments of the present invention and are not limiting of the specification and claims in any way.

EXAMPLE 1

2',4"-bistrimethylsilyl-9-oxime Erythromycin A

9-Oxime erythromycin A (7.5 g) was suspended in 70 mL acetonitrile and hexamethyldisilazane (4.8 g). The mixture was stirred at room temperature for 16 hours. The mixture was concentrated until crystallization began. The mixture was stirred for an additional 30 min and filtered to give 6.8 g of the title product as a white crystalline solid.

$^{13}$C NMR (CDCl$_3$) δ0.8 (—SiMe$_3$), 0.9 (—SiMe$_3$), 40.9 (—N(CH$_3$)$_2$), 49.7 (3"-OCH$_3$), 170.6 (C=O), 176.1 (C=N) MS (CIMS): 892 (MH$^+$).

EXAMPLE 2

2',4"-bistrimethylsilyl-9-[O-(2,6-dichlorobenzoyl) oxime] Erythromycin A

To a solution of the product from Example 1 (25 g) in CH$_2$Cl$_2$ (125 mL) and triethylamine (10 mL) was added dimethylaminopyridine (200 mg) and 2,6-dichlorobenzoyl chloride (8 g). The mixture was stirred at room temperature for 5 hours. Water (100 mL) was added and the mixture was diluted with methyl-t-butyl ether. The aqueous layer was removed and the organic layer was washed with a dilute NaOH solution followed by a saturated NaCl solution. The organic layer was dried (MgSO$_4$) and evaporated to dryness. The residue was dissolved in 25% ethyl acetate/heptane and loaded on a small silica gel pad. Elution with 10% ethyl acetate/heptane with 1% triethylamine gave fractions containing pure product. The fractions were combined and evaporated to give 11.4 g of the title product as a white solid.

$^{13}$C NMR (CDCl$_3$) δ0.8 (2×—SiMe$_3$), 40.8 (—N(CH$_3$)$_2$), 49.5 (3"-OCH$_3$), 163.0 (C=O), 176.0 (C=O), and 179.6 (C=N). MS (CIMS): 1065 (MH$^+$).

EXAMPLE 3

2',4"-bistrimethylsilyl-9-[O-2,6-(dimethoxybenzoyl) oxime] Erythromycin A

To a solution of 2',6"-bistrimethylsilyl-9-oxime erythromycin A from Example 1 (10 g) in CH$_2$Cl$_2$ (50 mL) and pyridine (5 mL) was added dimethylaminopyridine (200 mg) and 2,6-dimethoxybenzoyl chloride (3.0 g). The mixture was stirred at room temperature for 1 hour. Methylene chloride was removed under vacuum and the residue was dissolved in methyl-t-butyl ether (200 mL). Water (100 mL) was added and the pH of the solution was adjusted to 13 using 50% aqueous NaOH. The organic layer was separated, washed with water (3×150 mL), dried (MgSO$_4$) and evaporated to dryness to give the title compound (10.5 g) as a white solid.

$^{13}$C NMR (CDCl$_3$) δ0.7 and 0.8 (2×—SiMe$_3$), 40.8 (—N(CH$_3$)$_2$), 49.5 (3"-OCH$_3$), 55.4 and 55.9 (2×—OCH$_3$), 164.3 (C=O), 175.8 (C=O), and 178.2 (C=N). MS (CIMS): 1057 (MH$^+$).

EXAMPLE 4

2',4"-bistrimethylsilyl-9-[O-(2,6-dichlorobenzoyl) oxime]-6-O-methyl Erythromycin A A solution of 2',4"-bistrimethylsilyl-9-[O-(2,6-dichlorobenzoyl)oxime erythromycin A from Example 2 (1.0 g) in dimethylsulfoxide (5 mL) and tetrahydrofuran (5 mL) was cooled to 7° C. To this mixture, methyl iodide (0.15 mL) and 85% potassium hydroxide powder (120 mg) were added. The mixture was stirred at 5° C.–15° C. for 1.5 hours. To the resulting mixture, a 40% aqueous methylamine solution (1 mL) and water (10 mL) were added. The mixture was extracted with methyl-t-butyl ether (2×50 mL). The organic layer was washed with water (2×30 mL) and dried (MgSO$_4$). The solvent was evaporated in vacuo to dryness to give the title compound (850 mg) as a white solid. The crude title product was purified by silica gel column chromatography using heptane/ethyl acetate/triethyl amine (6/4/0.5). MS: (MH$^+$).

$^{13}$C NMR (CDCl$_3$) δ0.8 and 0.9 (2×—SiMe$_3$), 40.8 (—N(CH$_3$)$_2$), 49.5 (3"-OCH$_3$), 51.0 (6-OMe), 164.5 (C=O), 175.6 (C=O), and 179.5 (C=N). MS (CIMS): 1117 (MK$^+$).

EXAMPLE 5

2',4"-bistrimethylsilyl-9-[O-(2,6-dimethoxybenzoyl) oxime]-6-O-methyl Erythromycin A A solution of 2',4"-bistrimethylsilyl-9-[O-(2,6-dimethoxybenzoyl)oxime erythromycin A from Example 3

(3.0 g) in dimethylsulfoxide (15 mL) and tetrahydrofuran (15 mL) was cooled to 7° C. To this mixture, a 2M solution of methyl bromide in t-butyl methyl ether (15 mL) and 85% potassium hydroxide powder (350 mg) were added. The mixture was stirred at 5° C.–7° C. for 4.5 hours. To the resulting mixture, 40% aqueous methylamine solution (2 mL) and water (120 mL) were added. The mixture was extracted with methyl-t-butyl ether (2×150 mL). The organic layer was washed with water (3×100 mL) and dried ($MgSO_4$). The solvent was evaporated in vacuo to dryness to give the title compound (2.3 g) as a white solid.

$^{13}C$ NMR ($CDCl_3$) δ0.8 and 1.0 (2×—$SiMe_3$), 40.9 (—$N(CH_3)_2$), 49.6 (3"-$OCH_3$), 50.3 (6-OMe), 55.6 (2×—$OCH_3$), 157.3 (C=O), 175.6 (C=O), and 176.0 (C=N).

EXAMPLES 6 AND 7

6-O-Methyl-9-Oxime Erythromycin A

To a solution of 2',4"-bistrimethylsilyl-9-[O-(2,6-dichlorobenzoyl)oxime]-6-O-methyl erythromycin A from Example 4 (250 mg) in MeOH (8 mL) was added a solution of potassium carbonate (200 mg) in water (1 mL). The mixture was heated at 45° C.–50° C. for 21 hours. The solution was cooled to room temperature and the crystalline solid 6-O-methyl erythromycin A (35 mg) was filtered. The mother liquor was concentrated to give additional (65 mg) product as determined by NMR. (See Table below).

To a solution of A 2',4"-bistrimethylsilyl-9-[O-(2,6-dimethoxybenzoyl)oxime]-6-O-methyl erythromycin A from Example 5 (2 g) in MeOH (25 mL) was added a solution of potassium carbonate (1 g) in water (2 mL). The mixture was heated at 55° C. for 62 hours. The solution was cooled to room temperature and solid organic impurities were removed by filtration. The filtrate was evaporated to give 6-O-methyl-9-Oxime Erythromycin A as determined by NMR (see Table below).

$^1H$ and $^{13}C$ NMR Assignments for 6-O-Methyl-9-Oxime Erythromycin A

| Position | $^{13}C$ (ppm)[a] | $^1H$ (ppm)[b] |
|---|---|---|
| Erythronolide | | |
| 1 | 175.8 | — |
| 2 | 44.9 | 2.93 |
| 2-Me | 16.0 | 1.19 |
| 3 | 78.9 | 3.78 |
| 4 | 38.7 | 2.05 |
| 4-Me | 9.2 | 1.09 |
| 5 | 80.4 | 3.70 |
| 6 | 79.0 | — |
| 6-Me | 20.1 | 1.47 |
| 7 | 37.1 | 159, 1.51 |
| 8 | 25.3 | 3.81 |
| 8-Me | 19.0 | 0.98 |
| 9 | 169.9 | — |
| 10 | 32.9 | 2.50 |
| 10-Me | 12.1 | 1.00 |
| 11 | 70.5 | 3.70 |
| 12 | 40.2 | 1.62 |
| 12-Me | 9.1 | 0.84 |
| 13 | 75.0 | 5.45 |
| 14 | 25.8 | 1.70, 1.47 |
| 15 | 10.5 | 0.88 |
| OMe | 51.2 | 3.13 |
| Desosamine | | |
| 1' | 102.7 | 4.46 |
| 2' | 71.1 | 3.21 |
| 3' | 65.4 | 2.43 |
| 4' | 28.8 | 1.66, 1.22 |
| 5' | 68.6 | 3.50 |
| 6' | 21.5 | 1.23 |
| NMe2 | 40.3 | 2.29 |
| Cladinose | | |
| 1" | 96.1 | 4.95 |
| 2" | 35.0 | 2.37, 1.59 |
| 3" | 72.7 | — |
| 3'-Me | 21.5 | 1.24 |
| 4" | 78.0 | 3.03 |
| 5" | 65.7 | 4.04 |
| 6" | 18.7 | 1.30 |
| OMe | 49.5 | 3.33 |

[a]Relative to CDCl3 assigned as 77.0 ppm.
[b]Relative to TMS.

What is claimed is:

1. A process of preparing 6-O-methyl erythromycin A comprising the steps of:
   a) benzoylating 9-oxime erythromycin A to form a 9-oximebenzoyl erythromycin A derivative;
   b) protecting the 2'-hydroxyl group of the 9-oximebenzoyl erythromycin A derivative to form a 2' protected -9-oximebenzoyl erythromycin A derivative;
   c) methylating the 2',-protected-9-oximebenzoyl erythromycin A derivative to form a 2',-protected-6-O-methyl-9-oximebenzoyl erythromycin A derivative;
   d) removing the benzoyl and O-protecting groups from the 2'-protected -6-O-methyl-9-oximebenzoyl erythromycin A derivative to form 6-O-methyl-9-oxime erythromycin A; and
   e) deoximating the 6-O-methyl-9-oxime erythromycin A to form 6-O-methyl erythromycin A.

2. The process of claim 1 wherein the 9-oxime erythromycin A is reacted with a benzoylating reagent of the formula RCOX, where X is halide and R is a di-substituted benzene.

3. The process of claim 2 wherein R is 2,6-dichlorobenzene, 2,6-dibromobenzene, 2,6-diiodobenzene, 2,6-dimethoxybenzene or 2,6-diethoxybenzene.

4. The process of claim 1 further comprising the step of O-protecting the 4"-hydroxyl group of the 9-oximebenzoyl erythromycin A derivative prior to step (c).

5. The process of claim 4 wherein the 9-oximebenzoyl erythromycin A derivative is reacted with a silylating reagent of the formula $$X-\underset{\underset{R^3}{|}}{\overset{\overset{R^1}{|}}{Si}}-R^2$$

where X is halide, and $R^1$, $R^2$, and $R^3$ are each independently hydrogen, lower alkyl, aryl, phenyl, phenyl substituted lower alkyl, cycloalkyl or alkenyl.

6. The process of claim 5 wherein all of $R^1$, $R^2$ and $R^3$ are methyl.

7. The process of claim 4 wherein the 9-oximebenzoyl erythromycin A derivative is reacted with hexamethyldisilazane.

8. The process of claim 1 wherein the 2'-protected-9-oximebenzoyl erythromycin A derivative is reacted with a methyl halide or methyl sulfate in the presence of a base.

9. The process of claim 8 wherein the methyl halide is methyl bromide or methyl iodide and the sulfate is dimethylsulfate or methyl-p-toluenesulfonate.

10. The process of claim 1 wherein the 2'-protected-6-O-methyl-9-oximebenzoylerythromycin A derivative of step (d) is reacted with aqueous methanolic potassium carbonate.

11. A compound of the structure (I),

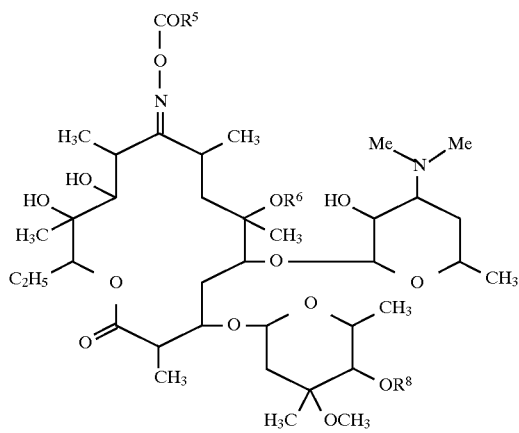

(I)

wherein $R^5$ is disubstituted benzene, $R^6$ is hydrogen or alkyl and $R^7$ and $R^8$ are each independently hydrogen, trimethylsilyl or an O-protecting group.

12. The compound of claim 11 wherein $R^6$ is methyl.

13. The compound of claim 11 wherein $R^5$ is 2,6-dichlorobenzene, 2,6-dibromobenzene, 2,6-diiodobenzene, 2,6-dimethoxybenzene or 2,6-diethoxybenzene.

14. The compound of claim 11 where both $R^7$ and $R^8$ are trimethylsilyl.

* * * * *